United States Patent
Tsuchiya et al.

(10) Patent No.: US 7,507,212 B2
(45) Date of Patent: Mar. 24, 2009

(54) ULTRASONIC TREATMENT DEVICE WITH MIST SUCTIONING STRUCTURE

(75) Inventors: Tomoyuki Tsuchiya, Tokyo (JP); Hideto Yoshimine, Tokyo (JP)

(73) Assignee: Olympus Corporation (JP)

( * ) Notice: Subject to any disclaimer, the term of this patent is extended or adjusted under 35 U.S.C. 154(b) by 530 days.

(21) Appl. No.: 11/116,520

(22) Filed: Apr. 28, 2005

(65) Prior Publication Data
US 2005/0245823 A1 Nov. 3, 2005

(30) Foreign Application Priority Data
Apr. 28, 2004 (JP) ............... 2004-134376

(51) Int. Cl.
*A61N 7/00* (2006.01)
*A61B 17/20* (2006.01)

(52) U.S. Cl. ............................... 601/2; 604/22

(58) Field of Classification Search ............ 601/2; 604/22, 27; 606/1, 127, 128
See application file for complete search history.

(56) References Cited

U.S. PATENT DOCUMENTS 5,163,433 A   11/1992   Kagawa et al.
5,211,625 A *  5/1993   Sakurai et al. ............... 604/22
5,391,144 A *  2/1995   Sakurai et al. ............... 604/22

FOREIGN PATENT DOCUMENTS

| EP | 0 635 978 | 1/1995 |
| EP | 0 645 987 | 1/1995 |
| EP | 1 025 806 A1 | 8/2000 |
| WO | WO 99/15120 | 4/1999 |
| WO | WO 99/29241 | 6/1999 |

OTHER PUBLICATIONS

Search Report issued by European Patent Office on Jul. 27, 2005 in connection with corresponding application No. EP 05 00 9329.

* cited by examiner

*Primary Examiner*—Eric F Winakur
(74) *Attorney, Agent, or Firm*—Ostrolenk, Faber, Gerb & Soffen, LLP (57) ABSTRACT

An ultrasonic treatment device comprises a handpiece having an ultrasonic transducer and a long axial probe whose base end is connected with the transducer. The device further comprises a tubular inner sheath covering the probe and an outer sheath covering the inner sheath with a predetermined annular space left therebetween. The space between the sheaths is used as a suction path for mist. For the suction, the device further comprises a base-end sealing member made of an elastic material, disposed on a base-end side of the outer sheath and engaged detachably with the inner sheath to seal a gap formed with the inner sheath. A suction unit is disposed on the base-end side of the outer sheath. The suction unit sucks in mist to be generated when ultrasonic treatment is performed, through the suction path, and discharged outside.

16 Claims, 6 Drawing Sheets

ULTRASONIC TREATMENT DEVICE WITH MIST SUCTIONING STRUCTURE

CROSS REFERENCES TO RELATED APPLICATION

The present application relates to and incorporates by reference Japanese Patent application No. 2004-134376 filed on Apr. 28, 2004.

BACKGROUND OF THE INVENTION

1. Technical Field of the Invention

The present invention relates to an ultrasonic treatment device equipped with a handpiece in which an ultrasonic transducer is contained to generate ultrasonic vibration and an ultrasonic probe transmitting the generated ultrasonic vibration so that the device is used for treating tissue of a living body using the transmitted ultrasonic vibration.

2. Related Art

Ultrasonic treatment devices have now become a significant tool used during a surgical operation. One type of such an ultrasonic treatment device has been proposed by European Patent No. 0 645 987 B 1. The ultrasonic treatment device proposed therein is provided with a handpiece which contains an ultrasonic transducer, with which a base end of an elongated probe for transmitting ultrasonic wave is coupled. The probe has a distal end which is opposite in location to the base end and has a treatment piece to be applied to living body tissue for ultrasonic treatment. Ultrasonic vibration created by the ultrasonic transducer is transmitted to the treatment piece along the probe, so that living body tissue can be treated with the energy from the ultrasonic vibration In this ultrasonic treatment device, a long sheath is placed to cover the probe transmitting the ultrasonic wave. The sheath has a distal end not only reaching a position near the treatment piece but also forming an annular space formed with the probe at the position. An opening is formed in the side wall of the sheath. A suction tube is connected at this opening so that the sheath is linked to the suction tube. During an ultrasonic treatment performed with the treatment piece, mist is frequently generated from the treated portion, but this mist can be suctioned out through the suction tube.

However, in the above conventional ultrasonic treatment device, the suction tube is secured at a given distal-side position on the sheath. Such distal-side position is almost next to the treatment piece. Thus the suction tube tends to interfere with operations for a treatment and narrow a field of view during a surgical operation. Further, due to the location that the suction tube is near the treatment piece, the suction tube is likely to interfere with other treatment devices, thus lowering operator's operationality. Another drawback results from the fact that the suction tube is fixedly secured on the sheath. Such a fixed position of the suction tube sometimes makes it difficult to easily remove foreign bodies from the suction tube, even when the foreign bodies are packed in the inner path of the suction tube. In addition, washing the treatment device is difficult on account of such positioning of the suction tube.

SUMMARY OF THE INVENTION

In view of the foregoing difficulties, the present invention is made to suction mist generated during a surgical operation and to avoid the suction tube from being interfered with other devices.

As one aspect of the ultrasonic treatment device according to the present invention, there is provided an ultrasonic treatment device comprising: a handpiece having an ultrasonic transducer; a probe having a base end connected to the ultrasonic transducer; a tubular inner sheath covering the probe; an outer sheath having a base end and covering the inner sheath with a predetermined space left between both the sheaths, the space functioning as a suction path for mist; a base-end sealing member made of an elastic material, disposed on the base end of the outer sheath and engaged detachably with the inner sheath to seal a gap formed with the inner sheath; and a suction member disposed on a base-end side of the outer sheath, formed to communicate with the suction path formed between both the outer and inner sheaths, and configured to suck in the mist through the suction path.

As another aspect of the ultrasonic treatment device according to the present invention, there is provided an ultrasonic treatment device comprising: a handpiece having an ultrasonic transducer; a probe having a base end connected to the ultrasonic transducer; a tubular inner sheath covering the probe; an outer sheath having a base end and covering the inner sheath with a predetermined space left between both the sheaths, the space functioning as a first suction path for mist; a base-end sealing member made of an elastic material, disposed on a base-end side of the outer sheath and engaged detachably with the inner sheath to seal a gap formed with the inner sheath; a suction member disposed on a base-end side of the outer sheath, formed to communicate with the first suction path formed between both the outer and inner sheaths; and a distal-end sealing member made of an elastic material, disposed on a distal end of the outer sheath, and engaged detachably with the inner sheath to seal a gap formed with the inner sheath, wherein a hole is formed through the inner sheath at a predetermined position of the inner sheath, the predetermined position being nearer to the base end of the inner sheath than a touched position of the distal-end sealing member to the inner sheath, such that the hole connects a further gap between the distal end of the probe and the inner sheath and the first suction path, the further gap functioning as a second suction path for the mist, the probe has an elastic support member formed to provide an outer diameter and located at a position of the probe, the position corresponding to a node of ultrasonic vibration to be transmitted from the ultrasonic transducer via the probe, the inner sheath has an inner diameter smaller than the outer diameter of the elastic support member, and the hole of the inner sheath is located between the elastic support member and the distal-end sealing member.

DETAILED DESCRIPTION OF THE PREFERRED EMBODIMENTS

With reference to the accompanying drawings, ultrasonic treatment devices according to the present invention will now be described.

First Embodiment

In connection with FIGS. 1 to 5A and 5B, a first embodiment of the ultrasonic treatment device according to the present invention will now be described. By the way, the ultrasonic treatment device to be described has a relatively thin and long body as shown in FIG. 1, for instance, so that the direction toward the left in FIG. 1 is often referred to as a "distal end" or "distal end side (tip side)" and the direction toward the right in FIG. 1 is often referred to as a "base", "base end", or "base end side."

Figure 1:
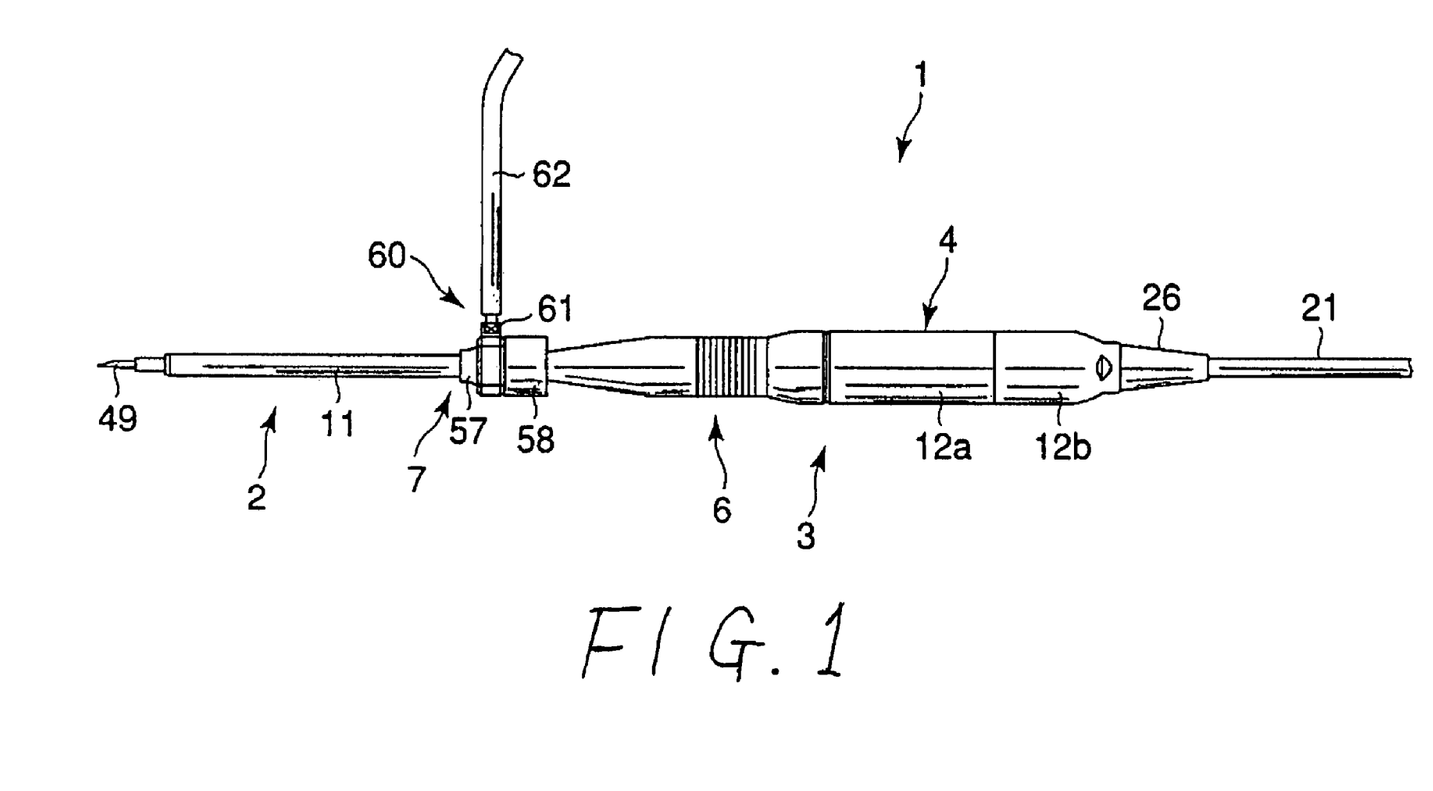
FIG. 1 is a side view outlining the external appearance of an ultrasonic treatment device according to a first embodiment of the present invention.

FIG. 1 shows the exterior appearance of an ultrasonic treatment device 1 according to the first embodiment. As shown, this ultrasonic treatment device 1 has, from its external appearance, a thin and long rod-like member 2 and a main body 3 coupled with a base of the rod-like member 2.

Figure 2:
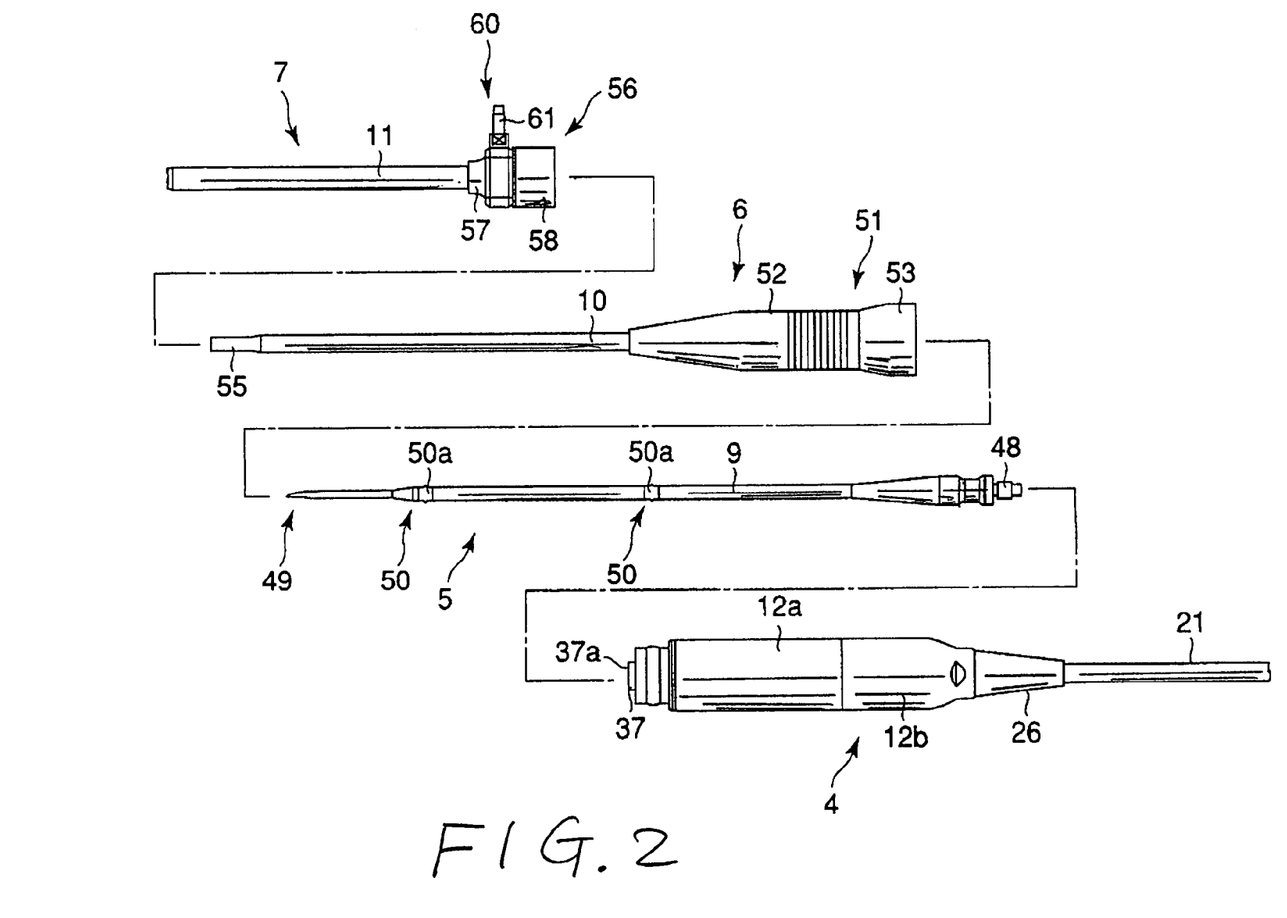
FIG. 2 is a side view explaining disassembled parts of the ultrasonic treatment device according to the first embodiment.

The ultrasonic treatment device 1 is, from a viewpoint of its assembling parts, composed of four components as shown in FIG. 2. Specifically, the four components are a handpiece 4, probe unit 5, inner sheath unit 6, and outer sheath unit 7, which are detachably assembled with each other.

Figure 3A:
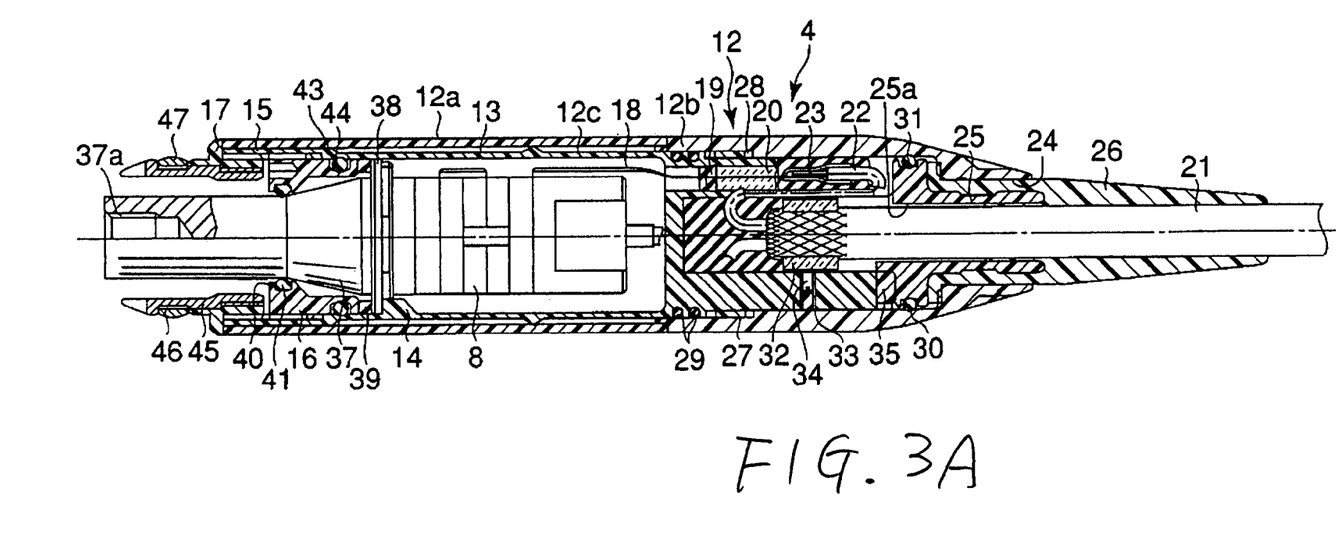
FIG. 3A is a longitudinally sectioned view showing the inner construction of a handpiece of an ultrasonic treatment device according to the first embodiment.

In the handpiece 4, an ultrasonic transducer 8 of bolt-clamped Langevin type (BLT) generating ultrasonic vibration is incorporated as shown in FIG. 3A. In the probe unit 5, a long rod-like probe 9 whose base end is connected to the ultrasonic transducer 8 is placed. This probe 9 transmits, toward its distal end, the ultrasonic vibration generated by the transducer 8. The inner sheath unit 6 includes a tubular inner sheath 10 to cover the probe 9. On the other hand, the outer sheath unit 7 includes an outer sheath 11 to cover the inner sheath 10.

FIG. 3A shows the inner construction of the handpiece 4, which has a cylindrical cover member 12. This cover member 12 includes a front case 12a, a rear case 12b, and an inner case 12c. An air layer 12 is formed between the distal-end portion of the front case 12a and the inner case 12c.

On the inner surface of the distal-end portion of the inner case 12c, a protrusion 14 to support the transducer 8 is formed. In addition, a female screw part 15 is formed at the distal end of the inner case 12c. This female screw part 15 is screwed with a support nut 16 which is inserted into the inner case 12c. A substantially tubular connection member 17 is loaded at the tips of both the inner case 12c and the front case 12a.

Meanwhile the ultrasonic transducer 8 is linked with an electrode plate 18 extending backward (rightward in FIG. 3A). This electrode plate 18 is supported by a support rubber member 19 so that the plate 18 is supported to the inner case 12c. A filler 20 is charged to hold the back of the support rubber member 19. Electric wires 22 extended from a cable 21 delivering current are solder-jointed to the electrode plate 18. Partial portions of the electric wires 22, which are subjected to the solder joint, are covered with an electric-insulative thermal-shrinking tube 23.

The rear case 12b has a base-end opening 24 at the base end thereof, through which a cable 21 is placed to pass. Between the cable 21 and the opening 24 of the rear case 12b, a breakage-preventing member 25 and a breakage-preventing rubber 26, which are formed into substantially tubes, are placed to be unified with the cable 21.

Meanwhile the inner case 12c includes an inversely-threaded rear-end screw part 27 formed on a partial outer surface on the rear end of the case 12c. To meet this rear-end screw part 27, a female screw part 28, which is an inverse screw to be screwed with the rear-end screw 27, is formed on a partial inner surface on the distal end of the rear case 12b. Thus the rear-end screw part 27 of the inner case 12c is screwed with the female screw part 28 of the rear case 12b to be fixedly linked with each other. O-rings 29 are placed between contact surfaces of both the rear-case 12b and the inner case 12c.

As shown in FIG. 3A, the breakage-preventing member 25 includes a partial outer surface on which an annular recess 30 is formed, the partial outer surface coming in contact with part of the inner surface of the rear case 12b. An O-ring 31 is placed in the recess 30 so as to seal a gap between both contact portions of the outer circumferential surface of the breakage-preventing member 25 and the inner circumferential surface of the rear case 12b.

On the distal end of the cable 21 is fixedly provided a ring-like removal-stopping member 32 whose diameter is larger than the inner diameter of a cylindrical opening 25a of the breakage-preventing member 25. At a predetermined position of the wall of the inner case 12c, which positionally corresponds to the removal-stopping member 32, screw holes 33 are drilled in the radial direction of the inner case 12c. Through each screw hole 33, a fixing screw 34 is inserted in a screwed manner to stop the rotation of the cable 21. Thus these fixing screws 34 enable the removal-stopping member 32 to be secured on the inner case 12c on mutually-opposite sides of the cable 21.

Figure 3B:
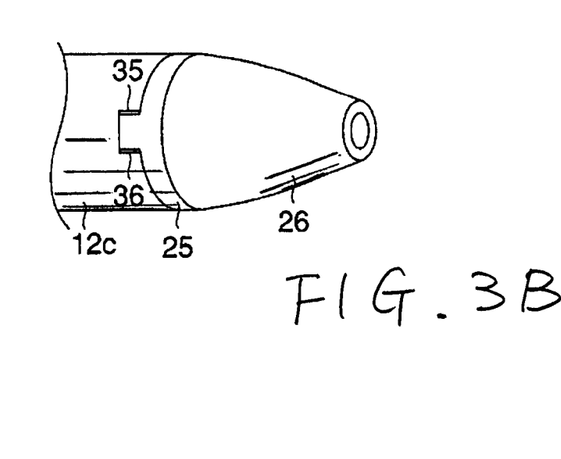
FIG. 3B is a perspective view illustrating an essential part of the engagement between a breakage-stopping member and an inner case, which are arranged in the handpiece.

As shown in FIG. 3B, a protrusion 35 is formed from the breakage-preventing member 25 in the axially forward direction of the case 12. The protrusion 35 is fitted into a recess 36 formed at the rear end of the inner case 12c, so that the breakage-preventing member 25 engages with the inner case 12c.

A substantially bell-shaped horn 37 is rigidly linked with the distal end of the ultrasonic transducer 8 in order to amplify the ultrasonic vibration therefrom. This horn 37 has a base end on which a flange 38 is formed. The ultrasonic transducer 8 is supported by allowing the flange 38 to be pinched between the transducer support protrusion 14 of the inner case 12c and a support nut 16. A rubber ring 39 is placed between the flange 38 and the support nut 16. On the distal end of the horn 37, a female screw part 37a is formed for linage with the probe.

A part of the inner surface of the distal end of the support nut 16 is inwardly protruded to form an annular protrusion 40. On the inner circumferential surface of this protrusion 40, a coaxial rubber ring 41 is formed integrally with the surface. The axial rubber ring 42 is subjected to pressing onto the outer circumferential surface of the horn 37. On the other hand, on the outer circumferential surface of the support nut 16, a groove 43 for accepting an O-ring is partly formed. An O-ring 44 is placed on this groove 43, resulting in sealing between the outer surface of the support nut 16 and the inner surface of the inner case 12c.

Further, the female screw part 15 on the inner surface of the distal end of the inner case 12c is subjected to being screwed with the connection member 17, as described. The connection member 17 has an inner circumferential surface part into which one end (base end) of a cylindrical reception member 45 is screwed for fixing. In addition, this reception member 45 has an outer circumferential surface on which an annular groove 46 is formed in a circumferential direction thereof, the groove 46 being located ahead of the connection member 17 in their axial directions. This groove 46 is loaded with an engagement ring 47 formed into a C-shape in section.

As shown in FIG. 2, the probe unit 5 has the probe 9, as described before, which has one end on the base end side thereof. On this base end, a male screw part 48 is formed. For realizing fixing, the male screw part 48 of the probe 9 is screwed into the female screw part 37a of the horn 37, which makes it possible the probe unit 5 is coupled with the handpiece 4 in a detachable manner.

To the distal end of the probe 9 is secured a treatment piece 49. At a predetermined intermediate position of the probe 9, which positionally corresponds to a node of ultrasonic vibration, an elastic support member 50 is loaded. The elastic support member 50 has ring-like protrusions 50a whose diameters are larger than that of the probe 9.

The inner sheath unit 6 is provided with the inner sheath 10, as described, and the base end of the inner sheath 10 has a handpiece connection portion 51 which is larger in diameter than a main part of the sheath 10. This handpiece connection portion 51 is provided with a cylindrical connecting main member 52 and a covering member 53.

Figure 4:
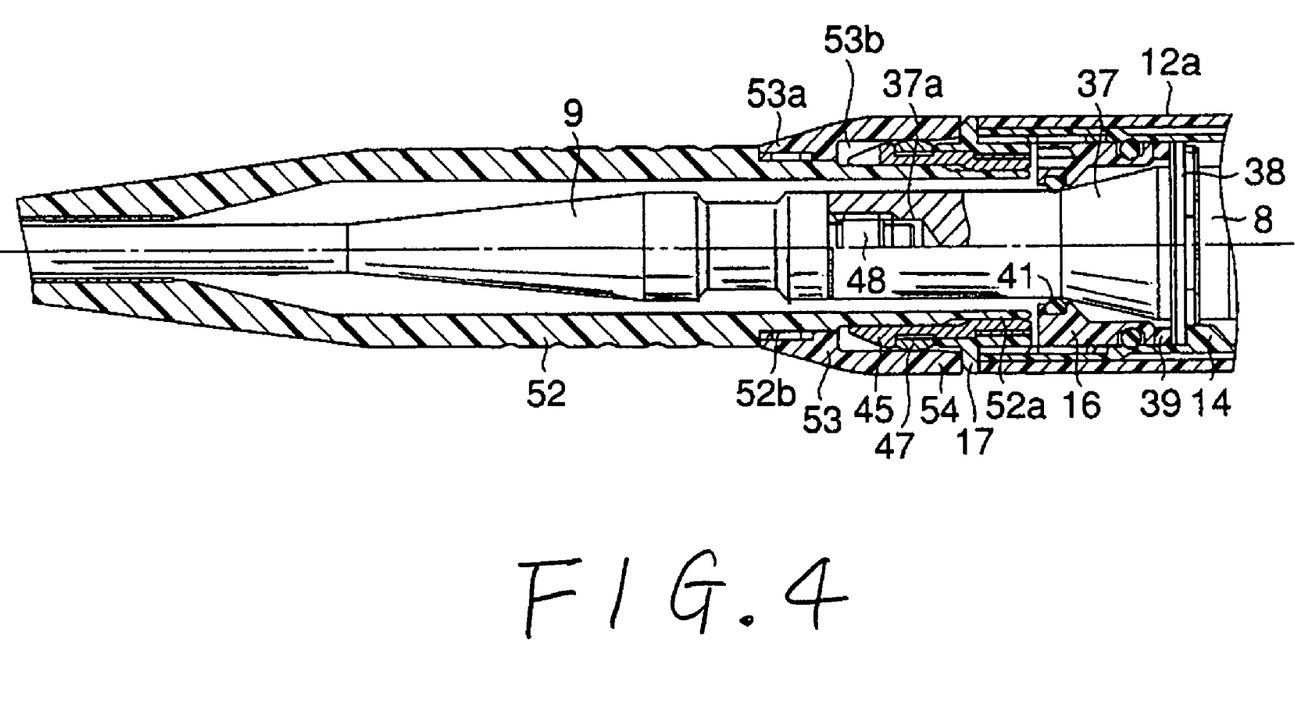
FIG. 4 is a longitudinally sectioned view illustrating the linkage between a horn and a probe, which are arranged in the ultrasonic treatment device according to the first embodiment.

As shown in FIG. 4, the connecting main member 52 includes a base end which has a small-diameter cylinder 52a to be inserted into the reception member 45 of the handpiece 4. A male screw part is formed on the outer circumferential surface of a distal end of the small-diameter cylinder 52a.

The covering member 53 has a distal end whose inner circumferential surface includes a female screw part 53a, with which the mail screw part 52b of the connecting main member 52 is screwed. By inserting and screwing the male screw part 52b of the connecting main member 52 into and with the female screw part 53a of the covering member 53, the covering member 53 can be coupled with a base end of the connecting main member 52 in the screwing fashion.

Moreover the distal end of the covering member 53 has a large-diameter connecting opening 53b, which is located rear the female screw part 53a and is able to accept the reception member 45 of the handpiece 4. This connecting opening 53b has an inner circumferential surface including an engagement part 54 which can be engaged detachably with the engagement ring 47 of the handpiece 4. When the handpiece connection portion 51 is coupled with the handpiece 4, the engagement part 54 is detachably engaged with the engagement ring 47 of the handpiece 4, while the small-diameter cylinder 52a of the connecting main member 52 is kept to be inserted in the reception member 45 of handpiece 4 which is concurrently inserted into the connecting opening 53b of the covering member 53. This allows the handpiece 4 to be coupled with the inner sheath unit 6 in a detachable manner. In this coupled attitude, the inner sheath 10 is located coaxially with the probe 9 and the protrusions 50a of the elastic support member 50 are elastically supported by the inner sheath 10 with the protrusions 50a pressed to the inner circumferential surface of the inner sheath 10, where the supported positions correspond to the positions of nodes of the ultrasonic vibration along the probe 9.

Figure 5A:
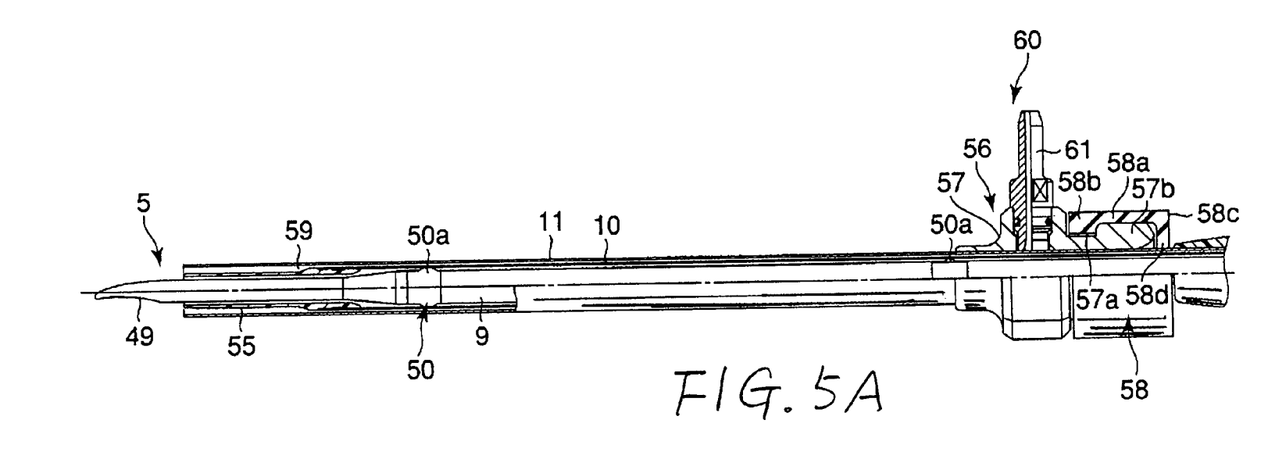
FIG. 5A is a partly sectioned side view showing the internal construction of a rod-like member arranged in the ultrasonic treatment device according to the first embodiment.
Figure 5B:
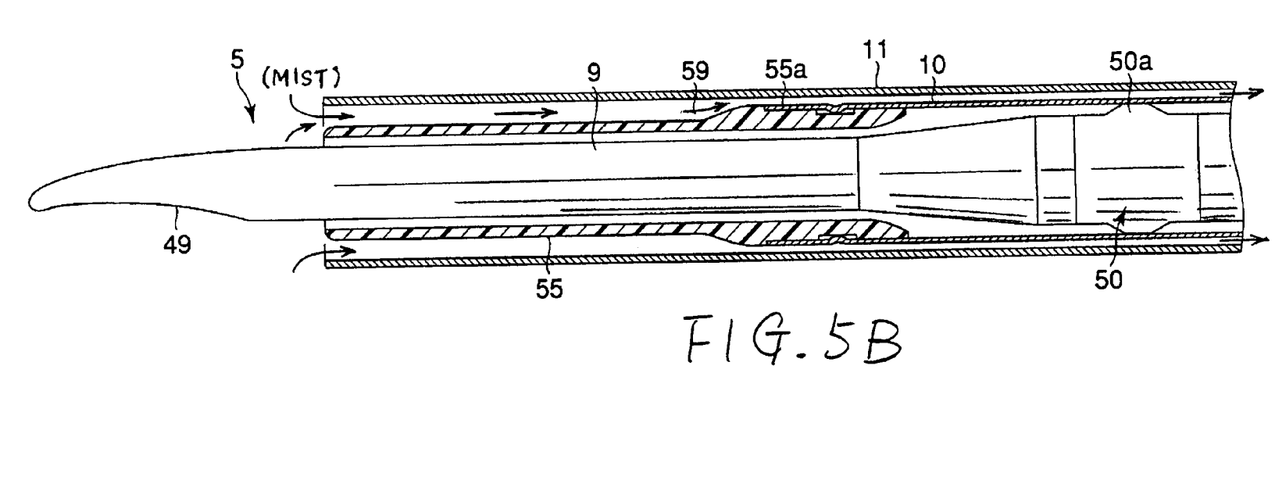
FIG. 5B is a longitudinally sectioned view illustrating an essential part of the internal construction of the distal end of of the rod-like member.

As shown in FIG. 5A, the inner sheath 10 has a distal end on which a cylindrical protective member 55 is arranged to protect the distal end of the probe 9. This proactive member 55 includes a base end of which outer circumferential surface has fit grooves 55a formed therealong, as shown in FIG. 5B. The fit grooves 55a accept the distal end of the inner sheath 10 such that the distal end is fit onto the fit grooves 55a.

The outer sheath unit 7 is provided with a large-diameter connecter 56 disposed at a base end of the outer sheath 11. As illustrated in FIG. 5A, the connecter 56 has a substantially cylindrical connecting main body 57 and a substantially cylindrical rubber member (elastic member) 58. The connecting main body 57 has a rear end portion having an outer circumferential surface, on which an annular engagement groove 57a is formed in the circumferential direction. This engagement groove 57a is located rearward next to a rubber-member loading portion 57b in the axial direction of the outer sheath unit 7 so that the loading portion 57b is built sharply.

The rubber member 58 has a cylindrical portion 58a to be loaded to the outer surface of the rubber-member loading portion 57b in a fit manner. This cylindrical portion 58a includes a distal end on which an engagement claw portion 58b is formed, the claw portion 58b detachably engaging with the engagement groove 57a of the connecting main body 57. The cylindrical portion 58a includes a rear end portion which is formed as a disk-like sealing portion 58c. This sealing portion 58c has an axial core opening formed to function as a sealing part 58d to seal a gap formed from the inner sheath 10 because of being pressed to the inner sheath 10.

In cases where the outer sheath unit 7 is assembled with the inner sheath unit 6, the connector 56 of the outer sheath unit 7 is arranged at the base end of the inner sheath 10 which kept inside the outer sheath 11. During this arrangement operation, the sealing part 58d of the sealing portion 58c is pressed onto the inner sheath 10 and fixed thereat, so that the sealing part 58d is able to engage/disengage with the outer surface of the inner sheath 10 so that a gap formed from the inner sheath 10 can be sealed. Thus the outer sheath 11 is sustained by the rubber member 58 coaxially with the inner sheath 10, resulting in that an annular and cylindrical sheath-to-sheath suction path 59 (i.e., a first suction path) is formed between the inner and outer sheaths 10 and 11.

Furthermore, there is formed a suction portion 60 connected with the connecting main body 57. This suction portion 60 is positioned before more than the engagement groove 57a and has a suction mouthpiece 61 protruded outwardly from the connecting main body 57. A suction path, which is formed in through the suction mouthpiece 61 as shown in FIG. 5A, is communicated to the sheath-to-sheath suction path 59. The other end of the suction mouthpiece 61, which is opposite to the connecting main body 57, is connected with a not-shown suction unit via a suction tube 62, which is shown in FIG. 1. Hence, when being driven, the suction unit is able to suck in mist through the sheath-to-sheath suction path 59 and mouthpiece 61.

The ultrasonic treatment device 1 according to the present embodiment will now be described in terms of the operations and advantages thereof.

For using this ultrasonic treatment device 1, the handpiece 4, probe unit 5, inner sheath unit 6, and outer sheath unit 7 are assembled with each other, so that as shown in FIG. 1, the ultrasonic treatment device 1 is build. During this assembly, the outer sheath unit 7 is assembled with the inner sheath unit 6, resulting in forming the suction paths passing the sheathto-sheath suction path 59 starting from the tip of the outer sheath 11 to the suction path realizing by the suction mouthpiece 61 (refer to FIGS. 5A and 5B). The suction tube 62 is then connected with the tip of the suction mouthpiece 61. This connection allows a not-shown suction unit to provide a suction force to the sheath-to-sheath suction path 59 of the ultrasonic treatment device 1 through the suction tube 62.

Driving the ultrasonic treatment device 1, the ultrasonic transducer 8 generates ultrasonic vibration. This ultrasonic vibration is subjected to amplification performed by the horn 37, and then transmitted to the probe 9. Thus when the tip of the probe 9, that is, the treatment piece 49, is touched to living body's tissue to be treated, so that ultrasonic treatment is carried out thereat.

In this treatment, the foregoing suction force is made active from the suction mouthpiece 61 to the sheath-to-sheath suction path 59. Mist to be generated during a surgical operation is thus sucked in from the tip of the sheath-to-sheath suction path 59 (i.e., the annular and cylindrical suction path left between the double tubes made of the inner and outer sheaths 10 and 11) and through the mouthpiece 61. Accordingly, whenever the mist is generated at treated regions during a surgical operation, the mist can be sucked in.

The present embodiment will thus provide the advantages as follows. At first, the mouthpiece 61 connected to the suction tube 62 is connected with the large-diameter connecter 56 located at the base end of the outer sheath unit 7. This eliminates the necessity of disposing the suction tube 62 at the distal end or its neighboring regions of the outer sheath unit 7, which will lead to obtaining a sufficient field of view for observation around the treatment piece 49 of the probe 9. Hence, for an ultrasonic treatment, a field of view for operator's observation at a region around the treatment piece 49 always becomes wider. In addition, the interferences of the suction tube 62 with other treatment devices can be obviated or can be lessened. Accordingly, a good mist-suction performance can be secured during a surgical operation.

Furthermore, the outer sheath 11 is sustained on the inner sheath 10 by the rubber member 58. This sustaining structure makes it easier to attach or detach the outer sheath 11 to or from the inner sheath 10, which will thus lead to selection between an outer sheath with no suction performance and the outer sheath 11 with the suction performance, as the need arises. For cleaning, the outer sheath 11 can be removed easily from the inner sheath 10, thus facilitating the cleaning operation, thus providing an improved usability of the ultrasonic treatment device 1.

Second Embodiment

Figure 6A:
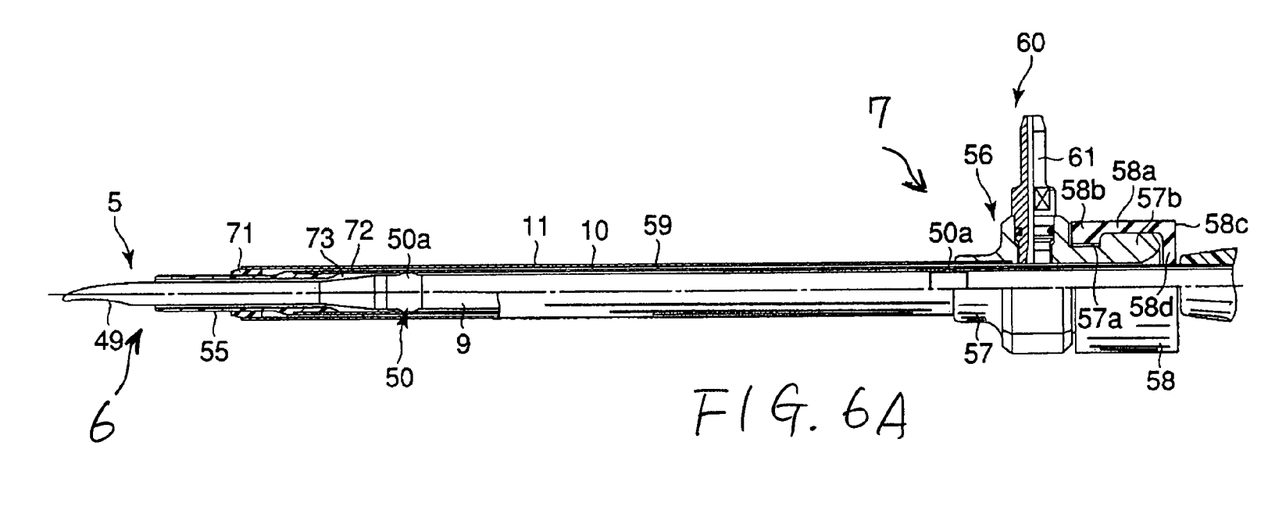
FIG. 6A is a partly sectioned side view illustrating the internal construction of a rod-like member of an ultrasonic treatment device according to a second embodiment of the present invention.
Figure 6B:
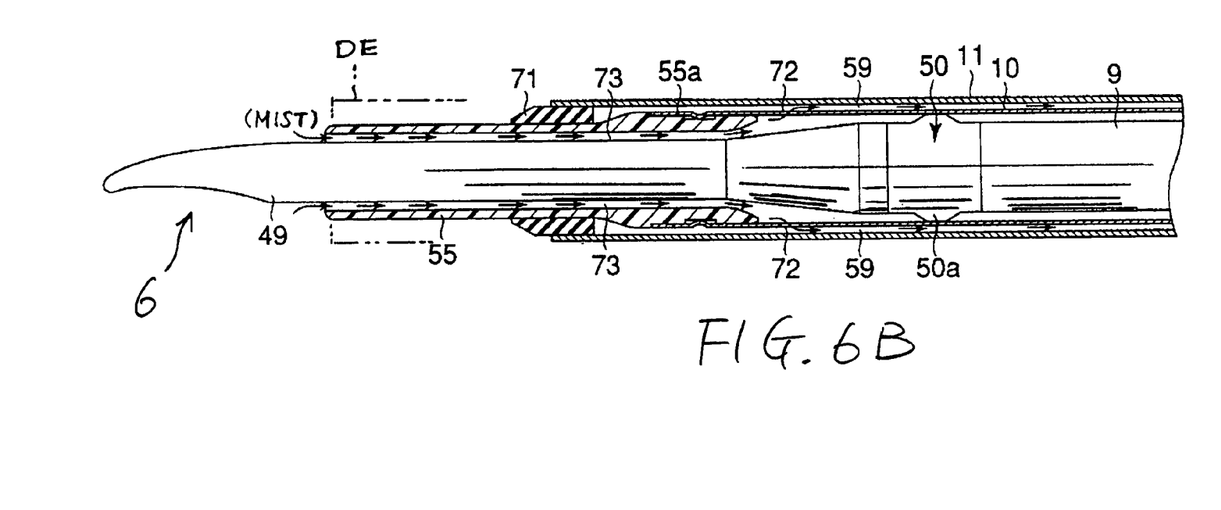
FIG. 6B is a longitudinally sectioned view illustrating an essential part of the internal construction of the distal end of the rod-like member.

Referring to FIGS. 6A and 6B, a second embodiment according to the ultrasonic treatment device of the present invention will now be described. In this second embodiment, the identical or similar components to those in the first embodiment are made reference by the same references in the first embodiment for the sake of simplified explanations.

The ultrasonic treatment device 1 according the second embodiment is able to have the same mist suctioning function as those in the first embodiment, but is different in structuring the suction paths from the first embodiment. The descriptions in this embodiment will be focused on this difference.

As shown in FIGS. 6A and 6B, in the second embodiment, a ring-like distal-end elastic member 71 is disposed on the tip of the outer sheath 11. This member 71 is made of rubber, for instance. This rubber member 71 is disposed such that is can be touched and detached to and from the inner sheath 10, so that the rubber member 71 is able to seal a gap formed with the inner sheath 10.

In assembling the outer sheath unit 7 with the inner sheath unit 6, the inner sheath 10 is inserted into the outer sheath 11 to locate the large-diameter connecter 56 of the outer sheath unit 7 at the base end of the inner sheath 10. In this located state, the distal end of the outer sheath 11 is fixedly located and sealed, because the distal-end elastic member 71 is pressed onto the protective member 55 on the inner sheath 10. Concurrently, at the base end of the outer sheath 11, the sealing part 58d of the rubber member 58 is pressed onto the inner sheath 10 and positionally fixed and sealed.

Hence, the distal-side and base-side ends of the sheath-to-sheath suction path 59 between the outer and inner sheaths 11 and 10 are sealed by the distal-end elastic member 71 and the rubber member 58. Both of the distal-end elastic member 71 and the rubber member 58 also allows the outer sheath 11 to be sustained coaxially with the inner sheath 10.

In addition, as shown in FIG. 6B, the inner sheath 10 has one or more through-holes 72 connecting to the foregoing sheath-to-sheath suction path 59. The through-holes 72 are formed through the inner sheath 10 at predetermined positions thereof which are nearer to the base end of the inner sheath 10 than the touched position of the distal-end elastic member 71 to the inner sheath 10. Therefore, between the distal end of the probe 9 (that is, the treatment piece 59) and the inner sheath 10, a distal-end suction path (a second suction path) 73 communicating with the sheath-to-sheath suction path (a first suction path) 59 via the through-holes 72 are realized.

The operations and advantages gained by the ultrasonic treatment device 1 of the present embodiment will now be described.

In this device 1, assembling the inner sheath unit 6 with the outer sheath unit 7 creates the suction paths, which consist of the distal-end suction path 73 starting from the distal end of the inner sheath 10, the though-holes 72, the sheath-to-sheath suction path 59, and the suction mouthpiece 61 in this order.

Hence, when an ultrasonic treatment is performed, the suction tube 62 connected to a not-shown suction unit is connected to the suction mouthpiece 61, whereby a suction of mist from a treated region can be allowed. Specifically, the mist generated during a surgical operation is first suctioned into the distal-end suction path 73 via the distal end of the inner sheath 10, suctioned into the sheath-to-sheath suction path 59 between the inner and outer sheaths 10 and 11 via the through-holes 72, and then suctioned into the suction mouthpiece 61. Accordingly, the mist yielded during the surgical operation can be discharged outside the object to be treated.

As a result, like the first embodiment, the mouthpiece 61 connected to the suction tube 62 is connected with the large-diameter connecter 56 located at the base end of the outer sheath unit 7. This eliminates the necessity of disposing the suction tube 62 at the distal end or its neighboring regions of the outer sheath unit 7, which will lead to obtaining a sufficient field of view for observation around the treatment piece 49 of the probe 9. Hence, for an ultrasonic treatment, a field of view for operator's observation at a region around the treatment piece 49 always becomes wider. In addition, the interferences of the suction tube 62 with other treatment devices can be obviated or can be lessened.

The present embodiment provides an additional advantage. The distal-end suction path 73 which communicates with the sheath-to-sheath suction path 59 via the through-holes 72 is formed between the distal end of the probe 9 (i.e., the treatment piece 49) and the protective member 55 of the inner sheath 10. This eliminates the need for making the distal end of the outer sheath 11 extend down to a position near the treatment piece 49 of the probe 9. In other words, as the comparison between FIGS. 6B and 5B clearly shows, the tip of the outer sheath 11 in FIG. 6B is shorter than that in FIG. 5B.

Thus, as distinctive from FIG. 6B, a neighboring portion of the probe 9 to the treatment piece 49 (refer to a reference DE illustrating an imaginary contour of the probe 9) can be made smaller in its diameter. During an ultrasonic treatment, the tip of a not-shown electronic end scope can be located near the region shown by the reference DE, so that the end scope is able to observe the treatment carried out with the treatment piece 49. In the present embodiment, the size of tip of the probe 9 can be made smaller, as described, due to less structure around the treatment piece 49. As a result, an observation view from the end scope can be widened around the treatment piece 49, whereby a wider field of view can be provided for treatments.

Accordingly, when compared with the configurations of the present invention, the advantages from the foregoing various embodiments can be summarized as follows.

At first, the inner sheath 10 is converted by the outer sheath 11 to form a double tubing structure. Further, the distal ends of the sheaths 10 and 11 are sealed with the rubber member 58 and the base end of the outer sheath 11 is coupled with the suction mouthpiece 61 to form a suction path through the space between the sheaths 10 and 11. Accordingly, owing to the fact that the suction tube 62 (i.e., suction mouthpiece 61) is located on the base side of the outer sheath 11, a field of view for surgery's observation can be secured sufficiently, at least compared with the conventional. Such a location of the suction tube 62 is also helpful for avoiding interferences with other types of treatment devices.

By the way, the location of the suction mouthpiece 61 (i.e., suction tube 62) is not always limited to that explained in the foregoing embodiment. The significant matter is that the suction mouthpiece 61 does not exist at positions of the outer sheath 11 including the distal end position (the leftmost tip position of the outer sheath 11 shown in, for example, FIG. 2) or positions which are very close to the distal end position. One modification is that the suction mouthpiece 61 is located at the center of the outer sheath 11 in the axial direction thereof. Another modification is that the suction mouthpiece 61 is located at any position between the axial center and base of the outer sheath 10. Such modified examples are still advantages to the conventional and can still enjoy the foregoing advantages.

Second, for securing the outer sheath 11 on the inner sheath 10, the rubber member 58 connected to the outer sheath 11 is used, so that the rubber member 58, that is, the outer sheath 11 can easily be attached to the inner sheath 10 in a detachable fashion. It is also easily selected whether the suction function is employed or not. Cleaning is also made simple. Further, the usability of the device can be improved.

Thirdly, as described using the second embodiment, the through-holes 72 are used to connect the sheath-to-sheath suction path (the first suction path) 59 and distal-end suction path (the second suction path) 73 so that the overall suction path is completed from the sheath tip to the suction mouthpiece 61. Hence, a space occupied by the outer sheath around the treatment piece 49 is made smaller in size (practically, diameter). In addition to enjoying the foregoing various advantages based on the first an second aspects, the construction using the first and second suction paths provides another advantage that the field of view for a surgeon is widened and is more enhanced.

The present invention may be embodied in other specific forms without departing from the spirit or essential characteristics thereof. The present embodiments and modifications are therefore to be considered in all respects as illustrative and not restrictive, the scope of the present invention being indicated by the appended claims rather than by the foregoing description and all changes which come within the meaning and range of equivalency of the claims are therefore intended to be embraced therein.

What is claimed is:

1. An ultrasonic treatment device comprising:
a handpiece having an ultrasonic transducer;
an ultrasonic probe having a base end operatively connected to the ultrasonic transducer for transmitting ultrasonic vibration;
a tubular inner sheath covering the probe;
an outer sheath having a base end and covering the inner sheath with a predetermined space left between both sheaths, the space functioning as a suction path for mist;
a base-end sealing member comprised of an elastic material, disposed on the base end of the outer sheath and engaged detachably with the inner sheath to seal a gap formed with the inner sheath;
and a suction member disposed on a base-end side of the outer sheath, formed to communicate with the suction path formed between both the outer and inner sheaths, and configured to suck in the mist through the suction path.

2. The ultrasonic treatment device according to claim 1, wherein a distal end of the suction path formed between the outer and inner sheaths is formed to be open.

3. The ultrasonic treatment device according to claim 2, wherein the probe has an elastic support member formed to provide an outer diameter and located at a position of the probe, the position corresponding to a node of ultrasonic vibration to be transmitted from the ultrasonic transducer via the probe and the inner sheath has an inner diameter smaller than the outer diameter of the elastic support member.

4. The ultrasonic treatment device according to claim 3, wherein
the elastic support member is supported by the inner sheath, with a protrusion of the elastic support member pressed to an inner circumferential surface of the inner sheath.

5. The ultrasonic treatment device according to claim 2, wherein the suction member has a suction mouthpiece formed to protrude at a position of the base end of the outer sheath and to detachably be connected with a suction tube extended from a suction source.

6. The ultrasonic treatment device according to claim 2, wherein the outer sheath is detachably coupled with the inner sheath.

7. The ultrasonic treatment device according to claim 1, comprising a distal-end sealing member comprised of an elastic material, disposed on a distal end of the outer sheath, and engaged detachably with the inner sheath to seal a gap formed with the inner sheath, wherein a hole is formed through the inner sheath at a predetermined position of the inner sheath, the predetermined position being nearer to the base end of the inner sheath than a touched position of the distal-end sealing member to the inner sheath, such that the hole connects a farther gap between the distal end of the probe and the inner sheath and the suction path, the farther gap functioning as a farther suction path.

8. The ultrasonic treatment device according to claim 7, wherein the probe has an elastic support member formed to provide an outer diameter and located at a position of the probe, the position corresponding to a node of ultrasonic vibration to be transmitted from the ultrasonic transducer via the probe and the inner sheath has an inner diameter smaller than the outer diameter of the elastic support member.

9. The ultrasonic treatment device according to claim 7, wherein the suction member has a suction mouthpiece formed to protrude at a position of the base end of the outer sheath and to detachably be connected with a suction tube extended from a suction source.

10. The ultrasonic treatment device according to claim 7, wherein the outer sheath is detachably coupled with the inner sheath.

11. An ultrasonic treatment device comprising:
   a handpiece having an ultrasonic transducer; an ultrasonic probe having a base end operatively connected to the ultrasonic transducer for transmitting ultrasonic vibration;
   a tubular inner sheath covering the probe;
   an outer sheath having a base end and covering the inner sheath with a predetermined space left between both sheaths, the space functioning as a first suction path for mist;
   a base-end sealing member comprised of an elastic material, disposed on a base-end side of the outer sheath and engaged detachably with the inner sheath to seal a gap formed with the inner sheath;
   a suction member disposed on a base-end side of the outer sheath, formed to communicate with the first suction path formed between both the outer and inner sheaths;
   and a distal-end sealing member comprised of an elastic material, disposed on a distal end of the outer sheath, and engaged detachably with the inner sheath to seal a gap formed with the inner sheath, wherein a hole is formed through the inner sheath at a predetermined position of the inner sheath, the predetermined position being nearer to the base end of the inner sheath than a touched position of the distal-end sealing member to the inner sheath, such that the hole connects a further gap between the distal end of the probe and the inner sheath and the first suction path, the further gap functioning as a second suction path for the mist, the probe has an elastic support member formed to provide an outer diameter and located at a position of the probe, the position corresponding to a node of ultrasonic vibration to be transmitted from the ultrasonic transducer via the probe, the inner sheath has an inner diameter smaller than the outer diameter of the elastic support member, and the hole of the inner sheath is located between the elastic support member and the distal-end sealing member.

12. The ultrasonic treatment device according to claim 11, wherein the suction member has a suction mouthpiece formed to protrude at a position of the base end of the outer sheath and to detachably be connected with a suction tube extended from a suction source.

13. The ultrasonic treatment device according to claim 11, wherein the outer sheath is detachably coupled with the inner sheath.

14. An ultrasonic treatment device comprising:
   a handpiece having an ultrasonic transducer;
   an ultrasonic probe operatively connected to the ultrasonic transducer for transmitting ultrasonic vibration;
   a first sheath covering an outer surface of the probe;
   a second sheath covering an outer surface of the first sheath;
   a first suction path formed between the first and second sheaths;
   and a suction mouthpiece disposed on a base-end side of the second sheath and formed to communicate with the first suction path, with
   a distal end of the probe being coupled with a treatment piece having a solid distal end, with ultrasonic vibration to be transmitted thereto from the ultrasonic transducer.

15. The ultrasonic treatment device according to claim 14, comprising a second suction path formed between the probe and the first sheath wherein the first sheath has a hole formed therethrough to allow both of the first and second suction paths to communicate with each other.

16. The ultrasonic treatment device according to claim 14, wherein the second sheath is detachable from the first sheath.

* * * * *